United States Patent
Li et al.

(10) Patent No.: US 11,459,369 B2
(45) Date of Patent: Oct. 4, 2022

(54) FUSION PROTEIN FOR ALPHA-MELANOCYTE STIMULATING HORMONE AND PREPARATION METHOD AND USE THEREOF

(71) Applicant: LANZHOU UNIVERSITY, Gansu (CN)

(72) Inventors: Hongyu Li, Gansu (CN); Meizhu Wang, Gansu (CN); Dejuan Zhi, Gansu (CN); Yang Li, Gansu (CN); Na Wang, Gansu (CN); Yiyao Liu, Gansu (CN); Yuejuan Pei, Gansu (CN); Meijuan Song, Gansu (CN); Yang Yang, Gansu (CN)

(73) Assignee: LANZHOU UNIVERSITY, Gansu (CN)

( * ) Notice: Subject to any disclaimer, the term of this patent is extended or adjusted under 35 U.S.C. 154(b) by 1071 days.

(21) Appl. No.: 15/780,577

(22) PCT Filed: Dec. 18, 2015

(86) PCT No.: PCT/CN2015/097783
§ 371 (c)(1),
(2) Date: May 31, 2018

(87) PCT Pub. No.: WO2017/101089
PCT Pub. Date: Jun. 22, 2017

(65) Prior Publication Data
US 2018/0371048 A1 Dec. 27, 2018

(51) Int. Cl.
| | |
|---|---|
| *C07K 14/685* | (2006.01) |
| *A61K 38/34* | (2006.01) |
| *C07K 19/00* | (2006.01) |
| *C12P 21/00* | (2006.01) |
| *C07K 7/06* | (2006.01) |
| *C07K 14/765* | (2006.01) |
| *C12N 15/81* | (2006.01) |

(52) U.S. Cl.
CPC .......... *C07K 14/685* (2013.01); *A61K 38/34* (2013.01); *C07K 7/06* (2013.01); *C07K 14/765* (2013.01); *C07K 19/00* (2013.01); *C12N 15/81* (2013.01); *C12P 21/00* (2013.01); *C07K 2319/00* (2013.01); *C12N 2510/02* (2013.01)

(58) Field of Classification Search
None
See application file for complete search history.

(56) References Cited

FOREIGN PATENT DOCUMENTS

| | | |
|---|---|---|
| CN | 101003568 A | 7/2007 |
| CN | 101233151 A | 7/2008 |
| CN | 102066421 A | 5/2011 |
| WO | 02/06316 A2 | 1/2002 |

OTHER PUBLICATIONS

Ahmed et al. ("Curbing Inflammation through Endogenous Pathways: Focus on Melanocortin Peptides," International Journal of Inflammation vol. 2013, Article ID 985815, 10 pages) (Year: 2013).*
Wilson ("Low permeability of the blood-brain barrier to nanomolar concentrations of immunoreactive alpha-melanotropin," Psychopharmacology (1988) 96: 262-266) (Year: 1988).*
Kratz et al. ("Albumin as a drug carrier: Design of prodrugs, drug conjugates and nanoparticles," Journal of Controlled Release 132 (2008) 171-183) (Year: 2008).*
Gump and Dowdy ("TAT transduction: the molecular mechanism and therapeutic prospects," TRENDS in Molecular Medicine vol. 13 No. 10, pp. 443-448) (Year: 2007).*
Chen et al. ("Fusion protein linkers: Property, design and functionality,"Advanced Drug Delivery Reviews 65 (2013) 1357-1369) (Year: 2013).*
International Search Report for PCT/CN2015/097783, dated Sep. 14, 2016.
European Search Report for EP Application No. 15910560.0 dated Nov. 7, 2018 (3 pages).
Banks et al., "Permeability of the Blood-Brain Barrier to Melancortins," Peptides, 1995, 16(6):1157-1161.
Dietz et al., "Peptide-Enhanced Cellular Internalization of Proteins in Neuroscience," Brain Research Bulletin, 2005, 68:103-114.
Fung et al., "Design of Cyclic and Other Templates for Potent and Selective Peptide α-MSH Analogues," Curr Opin Chem Biol., 2005, 9(4):352-358.
Murriel et al., "Influence of Protein Transduction Domains on Intracellular Delivery of Macromolecules," Expert Opin. Drug Deliv., 2006, 3(6):1-8.
Strohl, "Fusion Proteins for Half-Life Extension of Biologies as a Strategy to Make Biobetters," BioDrugs, 2015, 29:215-239.
Wang et al., "TAT-HSA-α-MSH Fusion Protein with Extended Half-Life Inhibits Tumor Necrosis Factor-α in Brain Inflammation of Mice," Applied Microbiology and Biotechnology, 2016, 100:5353-5361.

* cited by examiner

*Primary Examiner* — Christina Bradley
(74) *Attorney, Agent, or Firm* — Merchant & Gould P.C.

(57) ABSTRACT

Disclosed is a fusion protein for α-Melanocyte stimulating hormone, the fusion protein containing a protein transduction domain (PTD), a human serum albumin (HSA) and an α-Melanocyte stimulating hormone (α-MSH). Also disclosed are a method for preparing the fusion protein and a use thereof for inhibiting or treating central nervous system inflammations.

16 Claims, 1 Drawing Sheet
Specification includes a Sequence Listing.

SEQUENCE LISTING

<160> NUMBER OF SEQ ID NOS: 17

<210> SEQ ID NO 1
<211> LENGTH: 33

```
<212> TYPE: DNA
<213> ORGANISM: Artificial Sequence
<220> FEATURE:
<223> OTHER INFORMATION: DNA sequence of PTD

<400> SEQUENCE: 1
tacggtagaa agaagagaag acaaagaaga aga                                   33

<210> SEQ ID NO 2
<211> LENGTH: 11
<212> TYPE: PRT
<213> ORGANISM: Artificial Sequence
<220> FEATURE:
<223> OTHER INFORMATION: Amino acid sequence of PTD

<400> SEQUENCE: 2

Tyr Gly Arg Lys Lys Arg Arg Gln Arg Arg Arg
1               5                   10

<210> SEQ ID NO 3
<211> LENGTH: 1755
<212> TYPE: DNA
<213> ORGANISM: Artificial Sequence
<220> FEATURE:
<223> OTHER INFORMATION: DNA sequence of HSA

<400> SEQUENCE: 3
gatgcacaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtcagctgaa      180
aattgtgaca atcacttcca tccctttttt ggagacaaat tatgcacagt tgcaactctt      240
cgtgaaacct atggtgaaat ggctgactgt tgtgcaaaac aagaacctga gaaaatgaa       300 tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttacttttat gccccggaac tccttttctt tgctaaaagg       480
tataaagctg cttttacaga atgttgccaa gctgctgata agctgcctg cctgttgcca       540 aagctcgatg aacttcggga tgaagggaag gcttcgtctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg cttgaatgtg ctgatgacag gcggacctt       780 gccaagtata tctgtgaaaa tcaagattcg atctccagta aactgaagga atgctgtgaa      840
aaacctctgt tggaaaaatc ccactgcatt gccgaagtgg aaaatgatga atgcctgct       900 gacttgcctt cattagctgc tgatttttgtt gaaagtaagg atgtttgcaa aaactatgct     960
gaggcaaagg atgtcttcct gggcatgttt ttgtatgaat atgcaagaag gcatcctgat     1020
tactctgtcg tgctgctgct gagacttgcc aagcatatatg aaaccactct agagaagtgc    1080
tgtgccgctg cagatcctca tgaatgctat gccaaagtgt tcgatgaatt taaacctctt    1140
gtggaagagc tcagaatttt aatcaaacaa aattgtgagc tttttgagca gcttggagag    1200
tacaaattcc agaatgcgct attagttcgt tacaccaaga agtaccccca agtgtcaact    1260
ccaactcttg tagaggtctc aagaaaccta ggaaagtgg gcagcaaatg ttgtaaacat     1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
```

```
ttggtgaaca ggcgaccatg cttttcagct ctggaagtcg atgaaacata cgttcccaaa    1500
gagtttaatg ctgaaacgtt caccttccat gcagatatat gcacactttc tgagaaggag    1560
agacaaatca gaaacaaac tgcacttgtt gagcttgtga acacaagcc caaggcaaca     1620 aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gctta                                                      1755
```

<210> SEQ ID NO 4
<211> LENGTH: 585
<212> TYPE: PRT
<213> ORGANISM: Artificial Sequence
<220> FEATURE:
<223> OTHER INFORMATION: Amino acid sequence of HSA

<400> SEQUENCE: 4

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 5
<211> LENGTH: 39
<212> TYPE: DNA
<213> ORGANISM: Artificial Sequence
<220> FEATURE:
<223> OTHER INFORMATION: DNA sequence of alpha-MSH

<400> SEQUENCE: 5
tcttactcta tggagcactt tagatggggt aagccagtt                        39

<210> SEQ ID NO 6
<211> LENGTH: 13
<212> TYPE: PRT
<213> ORGANISM: Artificial Sequence
<220> FEATURE:
<223> OTHER INFORMATION: Amino acid sequence of alpha-MSH

<400> SEQUENCE: 6

Ser Tyr Ser Met Glu His Phe Arg Trp Gly Lys Pro Val
1               5                   10
```

<210> SEQ ID NO 7
<211> LENGTH: 1860
<212> TYPE: DNA
<213> ORGANISM: Artificial Sequence
<220> FEATURE:
<223> OTHER INFORMATION: DNA sequence of fusion protein
      PTD-HSA-L-alpha-MSH

<400> SEQUENCE: 7

```
tacggtagaa agaagagaag acaaagaaga agagatgcac acaagagtga ggttgctcat      60
cggtttaaag atttgggaga agaaaatttc aaagccttgg tgttgattgc ctttgctcag     120
tatcttcagc agtgtccatt tgaagatcat gtaaaattag tgaatgaagt aactgaattt     180
gcaaaaacat gtgttgctga tgagtcagct gaaaattgtg acaaatcact tcatacccct     240
tttggagaca aattatgcac agttgcaact cttcgtgaaa cctatggtga aatggctgac     300
tgttgtgcaa acaagaacc tgagagaaat gaatgcttct tgcaacacaa agatgacaac     360
ccaaacctcc cccgattggt gagaccagag gttgatgtga tgtgcactgc ttttcatgac     420
aatgaagaga cattttttgaa aaaatactta tatgaaattg ccagaagaca tccttacttt     480
tatgccccgg aactcctttt ctttgctaaa aggtataaag ctgcttttac agaatgttgc     540
caagctgctg ataaagctgc ctgcctgttg ccaaagctcg atgaacttcg ggatgaaggg     600
aaggcttcgt ctgccaaaca gagactcaag tgtgccagtc tccaaaaatt ggagaaaga     660
gctttcaaag catgggcagt agctcgcctg agccagagat ttcccaaagc tgagtttgca     720
gaagtttcca agtagtgac agatcttacc aaagtccaca cggaatgctg ccatggagat     780
ctgcttgaat gtgctgatga cagggcggac cttgccaagt atatctgtga aaatcaagat     840
tcgatctcca gtaaactgaa ggaatgctgt gaaaaacctc tgttggaaaa atcccactgc     900
attgccgaag tggaaaatga tgagatgcct gctgacttgc cttcattagc tgctgatttt     960
gttgaaagta aggatgtttg caaaaactat gctgaggcaa aggatgtctt cctgggcatg    1020
ttttgtatg aatatgcaag aaggcatcct gattactctg tcgtgctgct gctgagactt    1080
gccaagacat atgaaaccac tctagagaag tgctgtgccg ctgcagatcc tcatgaatgc    1140
tatgccaaag tgttcgatga atttaaacct cttgtggaag agcctcagaa tttaatcaaa    1200
caaaattgtg agcttttga gcagcttgga gagtacaaat tccagaatgc gctattagtt    1260
cgttacacca agaaagtacc ccaagtgtca actccaactc ttgtagaggt ctcaagaaac    1320
ctaggaaaag tgggcagcaa atgttgtaaa catcctgaag caaaaagaat gccctgtgca    1380
gaagactatc tatccgtggt cctgaaccag ttatgtgtgt tgcatgagaa aacgccagta    1440
agtgacagag tcaccaaatg ctgcacagaa tccttggtga acaggcgacc atgcttttca    1500
gctctggaag tcgatgaaac atacgttccc aaagagttta atgctgaaac gttcaccttc    1560
catgcagata tatgcacact ttctgagaag gagagacaaa tcaagaaaca aactgcactt    1620
gttgagcttg tgaaacacaa gcccaaggca acaaaagagc aactgaaagc tgttatggat    1680
gatttcgcag cttttgtaga gaagtgctgc aaggctgacg ataaggagac tgctttgcc    1740
gaggagggta aaaaacttgt tgctgcaagt caagctgcct taggcttagg aggtggaggt    1800
tctggaggtg gatctggttc ttactctatg gagcacttta gatggggtaa gccagtttaa    1860
```

<210> SEQ ID NO 8
<211> LENGTH: 619
<212> TYPE: PRT
<213> ORGANISM: Artificial Sequence
<220> FEATURE:
<223> OTHER INFORMATION: Amino acid sequence of fusion protein
      PTD-HSA-L-alpha-MSH

<400> SEQUENCE: 8

```
Tyr Gly Arg Lys Lys Arg Arg Gln Arg Arg Asp Ala His Lys Ser
1               5                   10                  15

Glu Val Ala His Arg Phe Lys Asp Leu Gly Glu Glu Asn Phe Lys Ala
                20                  25                  30

Leu Val Leu Ile Ala Phe Ala Gln Tyr Leu Gln Gln Cys Pro Phe Glu
            35                  40                  45

Asp His Val Lys Leu Val Asn Glu Val Thr Glu Phe Ala Lys Thr Cys
        50                  55                  60

Val Ala Asp Glu Ser Ala Glu Asn Cys Asp Lys Ser Leu His Thr Leu
65                  70                  75                  80

Phe Gly Asp Lys Leu Cys Thr Val Ala Thr Leu Arg Glu Thr Tyr Gly
                85                  90                  95

Glu Met Ala Asp Cys Cys Ala Lys Gln Glu Pro Glu Arg Asn Glu Cys
                100                 105                 110

Phe Leu Gln His Lys Asp Asp Asn Pro Asn Leu Pro Arg Leu Val Arg
            115                 120                 125

Pro Glu Val Asp Val Met Cys Thr Ala Phe His Asp Asn Glu Glu Thr
        130                 135                 140

Phe Leu Lys Lys Tyr Leu Tyr Glu Ile Ala Arg Arg His Pro Tyr Phe
145                 150                 155                 160

Tyr Ala Pro Glu Leu Leu Phe Phe Ala Lys Arg Tyr Lys Ala Ala Phe
                165                 170                 175

Thr Glu Cys Cys Gln Ala Ala Asp Lys Ala Ala Cys Leu Leu Pro Lys
            180                 185                 190

Leu Asp Glu Leu Arg Asp Glu Gly Lys Ala Ser Ser Ala Lys Gln Arg
        195                 200                 205

Leu Lys Cys Ala Ser Leu Gln Lys Phe Gly Glu Arg Ala Phe Lys Ala
        210                 215                 220

Trp Ala Val Ala Arg Leu Ser Gln Arg Phe Pro Lys Ala Glu Phe Ala
225                 230                 235                 240

Glu Val Ser Lys Leu Val Thr Asp Leu Thr Lys Val His Thr Glu Cys
                245                 250                 255

Cys His Gly Asp Leu Leu Glu Cys Ala Asp Asp Arg Ala Asp Leu Ala
            260                 265                 270

Lys Tyr Ile Cys Glu Asn Gln Asp Ser Ile Ser Ser Lys Leu Lys Glu
        275                 280                 285

Cys Cys Glu Lys Pro Leu Leu Glu Lys Ser His Cys Ile Ala Glu Val
        290                 295                 300

Glu Asn Asp Glu Met Pro Ala Asp Leu Pro Ser Leu Ala Ala Asp Phe
305                 310                 315                 320

Val Glu Ser Lys Asp Val Cys Lys Asn Tyr Ala Glu Ala Lys Asp Val
                325                 330                 335

Phe Leu Gly Met Phe Leu Tyr Glu Tyr Ala Arg Arg His Pro Asp Tyr
            340                 345                 350

Ser Val Val Leu Leu Leu Arg Leu Ala Lys Thr Tyr Glu Thr Thr Leu
        355                 360                 365

Glu Lys Cys Cys Ala Ala Ala Asp Pro His Glu Cys Tyr Ala Lys Val
        370                 375                 380

Phe Asp Glu Phe Lys Pro Leu Val Glu Glu Pro Gln Asn Leu Ile Lys
```

```
              385                 390                 395                 400
Gln Asn Cys Glu Leu Phe Glu Gln Leu Gly Glu Tyr Lys Phe Gln Asn
                405                 410                 415

Ala Leu Leu Val Arg Tyr Thr Lys Lys Val Pro Gln Val Ser Thr Pro
            420                 425                 430

Thr Leu Val Glu Val Ser Arg Asn Leu Gly Lys Val Gly Ser Lys Cys
        435                 440                 445

Cys Lys His Pro Glu Ala Lys Arg Met Pro Cys Ala Glu Asp Tyr Leu
    450                 455                 460

Ser Val Val Leu Asn Gln Leu Cys Val Leu His Glu Lys Thr Pro Val
465                 470                 475                 480

Ser Asp Arg Val Thr Lys Cys Cys Thr Glu Ser Leu Val Asn Arg Arg
                485                 490                 495

Pro Cys Phe Ser Ala Leu Glu Val Asp Glu Thr Tyr Val Pro Lys Glu
            500                 505                 510

Phe Asn Ala Glu Thr Phe Thr Phe His Ala Asp Ile Cys Thr Leu Ser
        515                 520                 525

Glu Lys Glu Arg Gln Ile Lys Lys Gln Thr Ala Leu Val Glu Leu Val
    530                 535                 540

Lys His Lys Pro Lys Ala Thr Lys Glu Gln Leu Lys Ala Val Met Asp
545                 550                 555                 560

Asp Phe Ala Ala Phe Val Glu Lys Cys Cys Lys Ala Asp Asp Lys Glu
                565                 570                 575

Thr Cys Phe Ala Glu Glu Gly Lys Lys Leu Val Ala Ala Ser Gln Ala
            580                 585                 590

Ala Leu Gly Leu Gly Gly Gly Ser Gly Gly Ser Gly Ser Tyr
        595                 600                 605

Ser Met Glu His Phe Arg Trp Gly Lys Pro Val
    610                 615

<210> SEQ ID NO 9
<211> LENGTH: 1824
<212> TYPE: DNA
<213> ORGANISM: Artificial Sequence
<220> FEATURE:
<223> OTHER INFORMATION: DNA sequence of fusion protein HSA-L-alpha-MSH

<400> SEQUENCE: 9
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttcca tacctttttt ggagacaaat tatgcacagt tgcaactctt     240
cgtgaaacct atggtgaaat ggctgactgt tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttacttttat gccccggaac tccttttctt tgctaaaagg     480
tataaagctg cttttacaga atgttgccaa gctgctgata agctgcctg cctgttgcca     540 aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag ggcggacctt     780
```

```
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg cagatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga aagtaccccca agtgtcaact     1260 ccaactcttg tagaggtctc aagaaaccta ggaaaagtgg gcagcaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca ggcgaccatg cttttcagct ctggaagtcg atgaaacata cgttcccaaa     1500
gagtttaatg ctgaaacgtt caccttccat gcagatatat gcacactttc tgagaaggag     1560
agacaaatca gaaacaaac tgcacttgtt gagcttgtga acacaagcc caaggcaaca     1620 aaagagcaac tgaaagctgt tatggatgat ttcgcagctt ttgtagagaa gtgctgcaag     1680
gctgacgata aggagacctg ctttgccgag gagggtaaaa aacttgttgc tgcaagtcaa     1740
gctgccttag gcttaggagg tggaggttct ggaggtggat ctggttctta ctctatggag     1800
cactttagat ggggtaagcc agtt                                             1824
```

<210> SEQ ID NO 10
<211> LENGTH: 608
<212> TYPE: PRT
<213> ORGANISM: Artificial Sequence
<220> FEATURE:
<223> OTHER INFORMATION: Amino acid sequence of fusion protein
      HSA-L-alpha-MSH <400> SEQUENCE: 10

```
Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
```

```
            165                 170                 175
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                    260                 265                 270

Ser Lys Leu Lys Glu Cys Cys Glu Lys Pro Leu Leu Glu Lys Ser His
                    275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                    340                 345                 350

Tyr Glu Thr Thr Leu Glu Lys Cys Cys Ala Ala Ala Asp Pro His Glu
                    355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                    420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575

Ala Ala Ser Gln Ala Ala Leu Gly Leu Gly Gly Gly Ser Gly Gly
            580                 585                 590
```

-continued

Gly Ser Gly Ser Tyr Ser Met Glu His Phe Arg Trp Gly Lys Pro Val
        595                 600                 605

<210> SEQ ID NO 11
<211> LENGTH: 10
<212> TYPE: PRT
<213> ORGANISM: Artificial Sequence
<220> FEATURE:
<223> OTHER INFORMATION: Linker peptide

<400> SEQUENCE: 11

Gly Gly Gly Gly Ser Gly Gly Gly Ser Gly
1               5                   10

<210> SEQ ID NO 12
<211> LENGTH: 30
<212> TYPE: DNA
<213> ORGANISM: Artificial Sequence
<220> FEATURE:
<223> OTHER INFORMATION: Linker peptide

<400> SEQUENCE: 12
ggaggtggag gttctggagg tggatctggt                                    30

<210> SEQ ID NO 13
<211> LENGTH: 48
<212> TYPE: DNA
<213> ORGANISM: Artificial Sequence
<220> FEATURE:
<223> OTHER INFORMATION: Primer for NFT1

<400> SEQUENCE: 13
tctctcgaga aaaggtacgg tagaaagaaa cgtagacaaa gacgtaga                48

<210> SEQ ID NO 14
<211> LENGTH: 44
<212> TYPE: DNA
<213> ORGANISM: Artificial Sequence
<220> FEATURE:
<223> OTHER INFORMATION: Primer for NFT2

<400> SEQUENCE: 14
gaaagaaacg tagacaaaga cgtagagatg cacacaagag tgag                    44

<210> SEQ ID NO 15
<211> LENGTH: 64
<212> TYPE: DNA
<213> ORGANISM: Artificial Sequence
<220> FEATURE:
<223> OTHER INFORMATION: Primer for R2

<400> SEQUENCE: 15
gctccataga gtaagaacca gatccacctc cagaacctcc acctcctaag cctaaggcag   60
cttg                                                                64

<210> SEQ ID NO 16
<211> LENGTH: 64
<212> TYPE: DNA
<213> ORGANISM: Artificial Sequence
<220> FEATURE:
<223> OTHER INFORMATION: Primer for R1

<400> SEQUENCE: 16
ttaaatggcc ggccggtacc ttaaactggc ttaccccatc taaagtgctc catagagtaa   60

```
gaac                                                           64

<210> SEQ ID NO 17
<211> LENGTH: 33
<212> TYPE: DNA
<213> ORGANISM: Artificial Sequence
<220> FEATURE:
<223> OTHER INFORMATION: Primer for NF

<400> SEQUENCE: 17
tctctcgaga aagggatgc acacaagagt gag                            33
```

FUSION PROTEIN FOR ALPHA-MELANOCYTE STIMULATING HORMONE AND PREPARATION METHOD AND USE THEREOF

This application is a U.S. National Stage Application under 35 U.S.C. § 371 of International Patent Application No. PCT/CN2015/097783, filed Dec. 18, 2015, the disclosures of all of which are hereby incorporated by reference in their entireties.

TECHNICAL FIELD

The present invention belongs to the field of genetic engineering of pharmacy. The present invention encompasses the application and preparation of α-Melanocyte stimulating hormone fusion protein.

BACKGROUND ART

Brain damage of vascular, inflammatory or traumatic brain injury causes activation cognitive dysfunction, which seriously affect our quality of life and work efficiency. Modern strategies for these diseases therapy point to the importance of global brain protection relative to protection of neurons. Indeed, not only neural cells but also other brain cells—astrocytes, oligodendrocytes, endothelial cells and microglia—need to be rescued after injury. α-MSH is an endogenous immunomodulatory peptide, and has been shown to exert anti-inflammatory, neurotrophic, anti-apoptotic and potential protective effects in brain damage. Compared with traditional anti-metabolisms immunosuppressant, α-MSH showed less side effects. It has been considered to be a promising drug candidate for anti-CNS disorders.

Immunomodulatory pathways of α-MSH: 1) immunomodulatory signaling of α-MSH is thought to via its receptors in immune cells including peripheral macrophages, monocytes and neutrophils, 2) and receptors distributed within CNS which triggers downstream anti-inflammatory neural pathways, 3) inflammation of the brain region can be suppressed by local expressed α-MSH through acting on receptors located in microglia and astrocytes, and also be suppressed by α-MSH generated from peripheral cells through cerebrospinal fluid circulation. Besides, the anti-inflammatory action of α-MSH has been proved in animal inflammation models including stimulate allergic dermatitis, allergic contact dermatitis, vasculitis, arthritis, eye inflammation, gastroenteritis, brain inflammation and allergic inflammation.

Mechanisms of the anti-inflammatory action in CNS: α-MSH inhibits activation of the transcription factor NF-κB which is the most important regulator molecule in inflammatory response. Consequently, α-MSH reduces the production of proinflammatory agents and adhesion molecules in brain cells after injury. Based on its anti-inflammatory action. It is well established that α-MSH interacting with its receptors exerts protective influences, nutrition and repair effects during brain damage.

α-MSH is a tridecapeptide derived from proopiomelanocortin, which is expressed in hypothalamus, pituitary and various peripheral tissue cells. The half-life of the full length peptide is only a few minutes in rat via iv administration. For this kind of therapeutic peptide, the glomerular filtration must be considered, thus it is necessary to modify structure of α-MSH or use other methods to prolong its half-life.

HSA is the most abundant plasma protein with 66 KDa in size and has an extraordinary long half-life of 19 days in human beings. Also it is the carrier of many endogenous metabolites and exogenous drugs. Additionally, it possess the characteristics of stability, compatibility, biodegradability, and lack of toxicity and immunogenicity. The above mentioned advantages make HSA a perfect fusion partner for therapeutic peptide and protein.

In the present invent, α-MSH was genetically fused to HSA which effectively increase the molecular weight of the desired fusion protein. In addition, a flexible glycine-serine rich linker between HSA and α-MSH was introduced to allow mobility of the α-MSH domain and enable the in vivo targeting of the fusion proteins.

Although it is proved that the half-life of therapeutic protein could be extended by fusion protein expression strategy, the structure design itself is a complicated procedure relative to numerous influencing factors. Thus it is well known that the simply combination of sequences is unable to achieve stable and efficient expression, and prolonged half-life of α-MSH fusion protein.

Furthermore, in an attempt to improve its ability of crossing the BBB, the fusion protein was genetically fused with PTD. PTD is an ideal transporter for crossing BBB found in recent years, which possess powerful carrier capable of transshipping large molecules that are 100 times higher than their own molecular weight. It has been proved that PTD-mediated transduction has capability to deliver macromolecular cross the cell membrane including exogenous proteins, DNA, RNA, chemical molecules, magnetic beads and liposomes, which could not be limited by size and variety of the cargos.

Based on the above thinking, the invention discloses a kind of α-Melanocyte stimulating hormone fusion protein with a unique amino acid sequence which can guarantee the stability of its high expression level in the host, while retain biological activity of α-MSH, can effectively across BBB and has a longer half-life in vivo. Additionally the present invention encompasses the application methods of treating, preventing, or ameliorating inflammatory CNS disorder using α-Melanocyte stimulating hormone fusion protein of the invention.

DISCLOSURE OF THE INVENTION

The aim of the present invention is to provide an α-MSH fusion protein which have prolonged circulating half-life, the ability of crossing the BBB, and stability of its high expression level in the host, also the therapeutic potential in the treatment of CNS inflammation.

A further object of the invention is to provide preparation methods of the described α-MSH fusion protein.

A further object of the invention is to provide recombinant expression vectors.

A further object of the invention is to provide a host expression system.

A further object of the invention is to provide a use of the described α-MSH fusion protein.

The described α-Melanocyte stimulating hormone fusion protein consists of PTD (Protein transduction domain), HSA (Human serum albumin) and α-MSH (α-Melanocyte stimulating hormone).

The described fusion protein further comprises a linker peptide L, and the HSA is genetically fused with the α-MSH through the linker peptide L.

An amino acid sequence of the linker peptide is GGGGSGGGSG (SEQ ID NO:11), encoded by a DNA sequence of GGAGGTGGAGGTTCTGGAGGTGGATCTGGT (SEQ ID NO:12).

The PTD is located in N-terminus of the described fusion protein, and the α-MSH is located in C-terminus of the described fusion protein. The fusion protein is expressed in term of PTD-HSA-L-α-MSH.

The described PTD has an amino acid sequence shown in SEQ ID NO:2, and a DNA encoding the amino acid sequence of the PTD has a sequence shown in SEQ ID NO:1.

The described HSA has an amino acid sequence shown in SEQ ID NO:4, and a DNA encoding the amino acid sequence of the HSA has a sequence shown in SEQ ID NO:3.

The described α-MSH has an amino acid sequence shown in SEQ ID NO:6, and a DNA encoding the amino acid sequence of the α-MSH has a sequence shown in SEQ ID NO:5.

The fusion protein has an amino acid sequence shown in SEQ ID NO:8, and a DNA encoding the amino acid sequence of the fusion protein has a sequence shown in SEQ ID NO:7.

The fusion protein is prepared by expression in cells of a yeast, and the yeast is methylotrophic *Pichia pastoris*.

A method for preparation of the α-MSH fusion protein according to the present application, wherein the method comprises steps of:

1) total gene synthesis of a sequence of α-MSH;
2) generating a sequence of PTD-HSA by PCR;
3) fusing the sequence of α-MSH from Step 1) and the sequence of PTD-HSA from step 2) by recombinant PCR, ligating a target fragment and a vector by In-fusion technology to obtain a recombinant yeast expression vector containing a DNA sequence of the α-MSH fusion protein; wherein the vector is pPinkα-HC.
4) transforming the recombinant yeast expression vector from Step 3) into *Escherichia coli* TOP10 competent cells, extracting and sequencing recombinant expression vector plasmids, and then transforming plasmids whose sequences have been proved correct into a host expression system for expression, thus obtaining the fusion protein, wherein the host expression system is methylotrophic *Pichia pastoris*.

A recombinant expression vector comprising the DNA sequence which encodes the amino acid sequence of the α-MSH fusion protein.

A host expression system comprising the abovementioned recombinant expression vector A use of the α-MSH fusion protein according to any one of Claims 1-7, 9 and 10 in preparation of drugs for inhibiting and treating inflammatory CNS (central nervous system) diseases and disorders.

THE BENEFICIAL EFFECTS OF THE INVENTION

1. With gene recombinant engineering technology, HSA, α-MSH and a flexible linker (linker peptide) between HSA and α-MSH have been genetically fused to generate the PTD-HSA-L-α-MSH fusion protein. While retaining stability and biological activity of α-MSH, the present disclosure has improved the circulating half-life of PTD-HSA-L-α-MSH and its ability of crossing the BBB, as well as the stability of their high expression level in the host.

2. The PTD has been introduced to the fusion protein to make the fusion protein able to cross the BBB, with the bioactivity of α-MSH retained. The fusion protein is utilized to treat, prevent or ameliorate inflammatory CNS disorders.

3. The α-MSH fusion protein of the invention can be used in preparation of drugs for inhibiting or treating inflammatory CNS disorders and related diseases.

DETAILED DESCRIPTION OF EMBODIMENTS

Experimental Instruments

Figure 1:
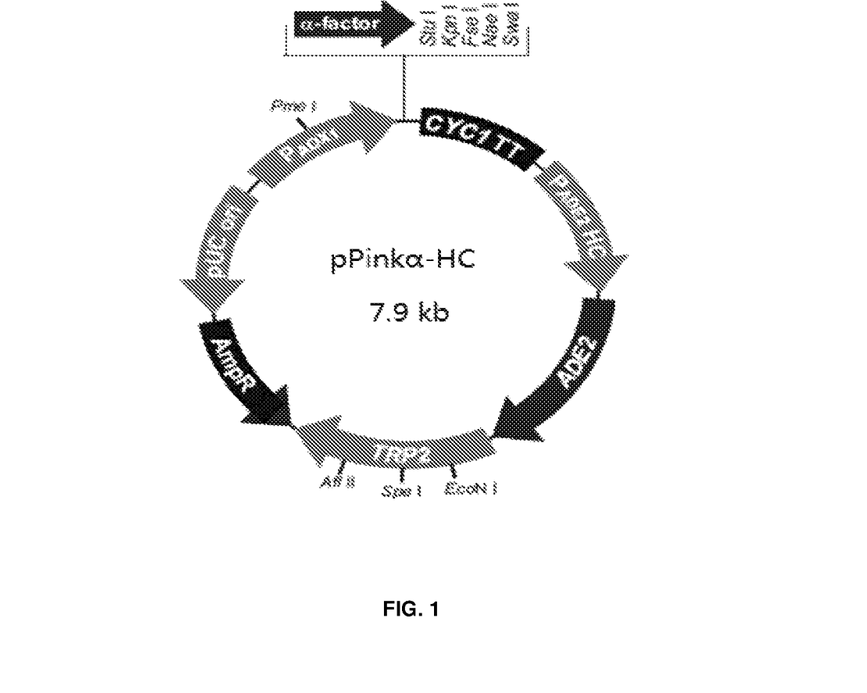
FIG. 1 showed the map of pPinkα-HC vector.
Figure 2:
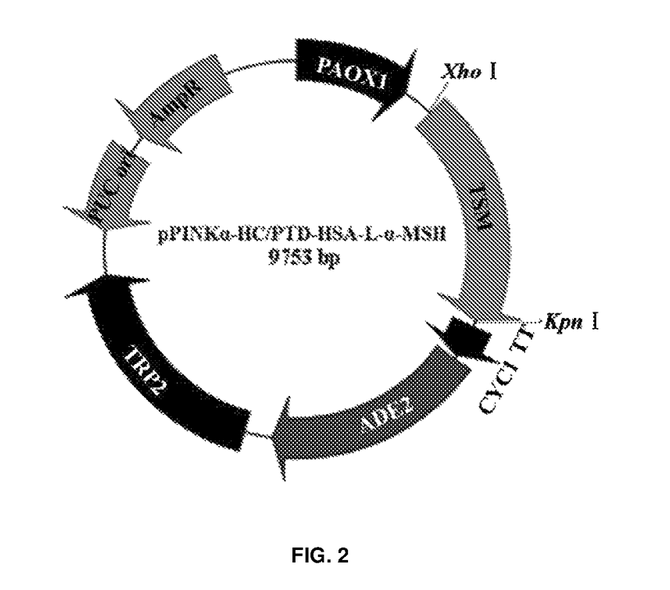
FIG. 2 showed the map of pPINKα-HC/PTD-HSA-L-α-MSH

Pipette, clean bench (An Tai), magnetic stirrer, microwave oven, high temperature steam sterilization pot, −80 low temperature refrigerator (Forma), ultra-pure water meter (Millipore), ice machine, centrifuge (Hitachi), HDB-PLUS constant temperature metal bath, HZQ-F16OA constant temperature oscillation incubator (Shanghai Yi Heng), PCR instrument (Applied Biosystems), centrifuge (Thermo), DYY-8B (Bo Le), Image electrophoresis Quant 300 gel imager (GE) etc.

Experimental Materials

Pipette, clean bench (An Tai), magnetic stirrer, microwave oven, high temperature steam sterilization pot, −80 low temperature refrigerator (Forma), ultra-pure water meter (Millipore), ice machine, centrifuge (Hitachi), HDB-PLUS constant temperature metal bath, HZQ-F16OA constant temperature oscillation incubator (Shanghai Yi Heng), PCR instrument (Applied Biosystems), centrifuge (Thermo), DYY-8B (Bo Le), Image electrophoresis Quant 300 gel imager (GE) etc.

Experimental Materials 1. restriction endonucleases StuI, KpnI, Xho I, AflII (NEB products, USA);
2. Plasmid Mini Preparation Kit, DNA purification kit, DNA Gel Extraction Kit (Sangon Biotech, China);
3. T4 DNA ligase Kit (Takara, Dalian, China);
4. pPinkα-HC, pcDNA3.1-HSA, *Pichia pastoris* strain, Infusion Cloning Kit (Invitrogen, USA);
5. *Escherichia coli* TOP10 (Tian Yuan biotech (Beijing) Co., Ltd.)
6. yeast extract and peptone (Oxford products, USA)
7. LB medium: Yeast extract 5 g, peptone 10 g, NaCl 10 g, dissolved in 1000 mL deionized water, and adjusted the pH to 7 with 1 mol/L NaOH, autoclave sterilization.
8. YPD medium: Yeast extract 10 g, peptone 20 g, Agar 20 g, dissolved in 900 mL deionized water, and then high pressure sterilization, after cooling, add 100 mL 20% of the right sugar sterilized by the filter sterilization.
9. YPDS medium: Yeast extract 10 g, peptone 20 g, sorbitol 182.2 g, dissolved in 900 mL deionized water, and then high pressure sterilization, after cooling, add 100 mL 20% of the right sugar sterilized by the filter sterilization.
10. BMGY liquid medium: 10 g yeast extract, peptone 20 g, YNB 13.4 g, glycerol 10 g, potassium phosphate 26.631 g, dissolved in 1000 mL double distilled water, and then high pressure sterilization, after cooling to room temperature, adjusting the pH to 6.4 and preserved at −4° C. refrigerator.
11. Preparation of 1% agarose gel: add 1 g agarose to 100 mL TAE buffer and heating to boiling until the agarose is melted completely by using microwave, then cool the mixture to room temperature and drop a small amount of ethidium bromide (EB), pour it into a glue tank with comb after sufficient mixing, finally pull the comb until completely solidification when cooled to room temperature.

EMBODIMENT

Embodiment 1

Generation of pPINKα-HC/PTD-HSA-L-α-MSH 1. primers used in generation of pPINKα-HC/PTD-HSA-L-α-MSH:

NFT1:
(SEQ ID NO: 13)
TCTCTCGAGAAAAGGTACGGTAGAAAGAAACGTAGACAAAGACGTAGA

NFT2:
(SEQ ID NO: 14)
GAAAGAAACGTAGACAAAGACGTAGA GATGCACACAAGAGTGAG

R2:
(SEQ ID NO: 15)
GCTCCATAGAGTAAGAACCAGATCCACCTCCAGAACCTCCACCTCCTAA
GCCTAAGGCAGCTTG

R1:
(SEQ ID NO: 16)
TTAAATGGCCGGCCGGTACCttaAACTGGCTTACCCCATCTAAAGTGCTC
CATAGAGTAAGAAC 2. First round PCR: pcDNA3.1-HSA vector was used as template with the forward primer NFT2 and the reverse primer R2. The reaction conditions are as follows: (1) degeneration at 94° C. for 5 min; (2) degeneration at 94° C. for 1 min; (3) renaturation at 55° C. for 30 s; (4) extension at 72° C. for 2 min; (5) return to step (2) and make 35 cycles; (6) extension at 72° C. for 5 min. The PCR products were analyzed by 1% agarose gel electrophoresis, and the results showed that the desired DNA bands were amplified about 1.8 kb in size.

3. Second round PCR: the first round PCR product was used as template with the forward primer NFT1 and the reverse primer R1. The reaction conditions are as follows: (1) degeneration at 94° C. for 5 min; (2) degeneration at 94° C. for 1 min; (3) renaturation at 55° C. for 30 s; (4) extension at 72° C. for 2 min; (5) return to step (2) and make 35 cycles; (6) extension at 72° C. for 5 min. The PCR products were analyzed by 1% agarose gel electrophoresis, and the results showed that the desired completely PTD-HSA-L-α-MSH DNA bands were amplified about 1.8 kb in size. The products was purified by DNA Gel Extraction Kit.

4. The pPinkα-HC vector was digested with Stu I and Kpn I, then product was purified by DNA purification kit. The PTD-HSA-L-α-MSH DNA was cloned into pPinkα-HC by In-Fusion technology. The recombinant DNA was transformed into competent cells of E. coli. The transformants were applied to the ampicillin resistance LB plate 37° C. with overnight incubation for screening positive clones. Finally, the recombinant DNA was confirmed by sequencing in Invitrogen and the correctly identified vector was named as pPINKα-HC/PTD-HSA-L-α-MSH.

Generation of pPINKα-HC/HSA-L-α-MSH 1. primers used in generation of pPINKα-HC/HSA-L-α-MSH:

NF:
(SEQ ID NO: 17)
TCTCTCGAGAAAAGGGATGCACACAAGAGTGAG

R2:
(SEQ ID NO: 15)
GCTCCATAGAGTAAGAACCAGATCCACCTCCAGAACCTCCACCTCCTAA
GCCTAAGGCAGCTTG

R1:
(SEQ ID NO: 16)
TTAAATGGCCGGCCGGTACCttaAACTGGCTTACCCCATCTAAAGTGCTCC
ATAGAGTAAGAAC 2. First round PCR: pcDNA3.1-HSA vector was used as template with the forward primer NF2 and the reverse primer R2. The reaction conditions are as follows: (1) degeneration at 94° C. for 5 min; (2) degeneration at 94° C. for 1 min; (3) renaturation at 55° C. for 30 s; (4) extension at 72° C. for 2 min; (5) return to step (2) and make 35 cycles; (6) extension at 72° C. for 5 min. The PCR products were analyzed by 1% agarose gel electrophoresis, and the results showed that the desired DNA bands were amplified about 1.8 kb in size.

3. Second round PCR: the first round PCR product was used as template with the forward primer NF and the reverse primer R1. The reaction conditions are as follows: (1) degeneration at 94° C. for 5 min; (2) degeneration at 94° C. for 1 min; (3) renaturation at 55° C. for 30 s; (4) extension at 72° C. for 2 min; (5) return to step (2) and make 35 cycles; (6) extension at 72° C. for 5 min. The PCR products were analyzed by 1% agarose gel electrophoresis, and the results showed that the desired completely HSA-L-α-MSH DNA bands were amplified about 1.8 kb in size. The products was purified by DNA Gel Extraction Kit.

4. The pPinkα-HC vector was digested with Stu I and Kpn I, then product was purified by DNA purification kit. The HSA-L-α-MSH DNA was cloned into pPinkα-HC by In-Fusion technology. The recombinant DNA was transformed into competent cells of E. coli. The transformants were applied to the ampicillin resistance LB plate 37° C. with overnight incubation for screening positive clones. Finally, the recombinant DNA was confirmed by sequencing in Invitrogen and the correctly identified vector was named as pPINKα-HC/HSA-L-α-MSH Expression of PTD-HSA-L-α-MSH and HSA-L-α-MSH in Host Cells pPINKα-HC/PTD-HSA-L-α-MSH vector and pPINKα-HC/HSA-L-α-MSH vector were linearized and transformed into host cells respectively. The transformants were applied to PAD plate 30° C. with 48 h incubation for screening positive clones. Then the selected positive clone was inoculated into BMGY medium, following by transferring to BMMY medium to induce expression of fusion protein for 96 h. Finally the supernatant was harvested by centrifugation at 1500×g for 5 min at 4° C., and the expression level of fusion protein was analyzed by SDS-PAGE. The strain with the highest expression level was selected as the engineering strain and stored at −80° C. PTD-HSA-L-α-MSH has the nucleotide sequence of SEQ ID NO:7, encoding the amino acid sequence shown in SEQ ID NO:8, and the molecular weight of it is about 70 KDa. HSA-L-α-MSH has the nucleotide sequence of SEQ ID NO:9, encoding the amino acid sequence shown in SEQ ID NO:10, and the molecular weight of it is about 69 KDa.

Embodiment 2

Validation of the Ability to Across BBB of PTD-HSA-L-α-MSH

Experimental Materials

1. Experimental Instruments

Syringes, pipette, centrifuge (Hitachi), ultra-pure water meter (Millipore), ultrasound, constant temperature Incubator (Shanghai YiHeng), Microplate reader (Thermo) etc.

HSA Elisa Kit (cygnustechnologies).

2. Experimental Animals 10 mice (18-22 g) were used in the experiment, and were purchased from Laboratory Animal Center of Lanzhou University.

3. Methods

Mice were housed in groups of at most five animals per cage with clean water and food available ad libitum. PTD-HSA-L-α-MSH or HSA-L-α-MSH were given at a dosage of 1 μm/kg through a single intravenous injection in 150 μL volume. Mice were anesthetized 6 h after drug administration. The hippocampal tissue was harvest and homogenized immediately. Finally the level of PTD-HSA-L-α-MSH or HSA-L-α-MSH in hippocampal tissue homogenate was tested by ELISA.

TABLE 1

| Results of ELISA test | |
| --- | --- |
| groups | PTD-HSA-L-α-MSH(ng/mL) |
| HSA-L-α-MSH | 0.06 ± 0.02 |
| PTD-HSA-L-α-MSH | 0.65 ± 0.01 |

The results listed in table one showed that the described PTD-HSA-L-α-MSH in the present invention possess the ability of across the BBB.

Embodiment 3

Neuroprotection of TAT-HSA-α-MSH on Experimental Brain Inflammation in Mice

Experimental Materials

1. Experimental Instruments

Syringes, pipette, centrifuge (Hitachi), ultra-pure water meter (Millipore), ultrasound, constant temperature Incubator (Shanghai YiHeng), Microplate reader (Thermo) etc.

TNF-a Elisa Kit (Dakewei, China).

2. Experimental Animals 20 mice (18-22 g) were used in the experiment, and were purchased from Laboratory Animal Center of Lanzhou University.

3. Methods

Mice were housed in groups of at most five animals per cage with clean water and food available ad libitum. PTD-HSA-L-α-MSH or HSA-L-α-MSH were given at a dosage of 1 μm/kg through a single intravenous injection in volume of 150 pt. Mice were anesthetized 6 h after drug administration. The hippocampal tissue was harvest and homogenized immediately. Finally the level of PTD-HSA-L-α-MSH or HSA-L-α-MSH in hippocampal tissue homogenate was tested by ELISA.

Lipopolysaccharide (LPS), a gram negative bacterial endotoxin, is the cell wall component of gram negative bacteria. Within the CNS, LPS challenge triggers central inflammatory responses, which results in releasing of proinflammatory mediators such as TNF-α. Therefore, to determine whether the described PTD-HSA-L-α-MSH can inhibit the production of pro-inflammatory factors in vivo, experimental brain inflammation of mouse induced by LPS was established, in which TNF-α was analyzed to detect the efficacy of PTD-HSA-L-α-MSH.

Mice were housed in groups of at most five animals per cage with clean water and food available ad libitum. The mice in control group were injected with 150 μL saline two times. The mice in LPS group were injected with 150 μL LPS at the dose of 5 mg/kg, and then injected with 150 μL saline. The mice in PTD-HSA-L-α-MSH+LPS group were injected with 150 μL LPS at the dose of 5 mg/kg, and then injected with 150 μL PTD-HSA-L-α-MSH at the dose of 1 μm/kg. The mice in α-MSH+LPS group were injected with 150 μL LPS at the dose of 5 mg/kg, and then injected with 150 μL α-MSH at the dose of 1 μm/kg. Mice were anesthetized 2 h after drug administration. The hippocampal tissue was harvest and homogenized immediately. Finally the level of TNF-α in hippocampal tissue homogenate was tested by ELISA.

TABLE 2

| TNF-α levels in hippocampal tissues tested by ELISA | |
| --- | --- |
| groups | TNF-α (pg/mg protein) |
| control | 14.8 ± 4.2 |
| LPS | 191.9 ± 9.1 |
| LPS + PTD-HSA-L-α-MSH | 38.3 ± 18.3 |
| LPS + α-MSH | 155.8 ± 10.3 |

Compared with the control group treated with saline, the level of TNF-α in LPS group was increased at 191.9 pg in per protein of homogenate, which indicated that the inflammation model was successfully established. Compared with LPS group, TNF-α increase was significantly inhibited in experimental brain inflammation mice after given PTD-HSA-L-α-MSH intraperitoneally at a single dose of 1 μm/kg in LPS+PTD-HSA-L-α-MSH group. In contrast, TNF-α could not be suppressed by α-MSH intraperitoneally injection in LPS+α-MSH group. The results indicated that PTD-HSA-L-α-MSH can potentially inhibit the CNS inflammation after i.p. administration. Taken together, the ability to cross the BBB, inhibition of CNS inflammation, make PTD-HSA-L-α-MSH a promising candidate therapeutic agent for treatment of neuro-inflammatory diseases.

The above is a detailed description of the present invention with a specific preferred embodiment, and it cannot be determined that the specific implementation of the present invention is confined to these embodiments. For the general technical personnel in the technical field of the invention, some simple deduction or replacement made with the concept of the invention should be regarded as the protection scope of the invention.

The invention claimed is:

1. An α-melanocyte stimulating hormone (α-MSH) fusion protein, wherein the α-MSH fusion protein comprises a protein transduction domain (PTD), a human serum albumin (HSA) and an α-MSH,
wherein the PTD is located at the N-terminus of the fusion protein, the α-MSH is located at the C-terminus of the fusion protein, and the HSA is genetically fused with the α-MSH through a peptide linker peptide (L), and
wherein the peptide linker comprises the amino acid sequence GGGGSGGGSG (SEQ ID NO: 11).

2. The α-MSH fusion protein according to claim 1, wherein the PTD comprises the amino acid sequence shown in SEQ ID NO: 2.

3. The α-MSH fusion protein according to claim 1, wherein the HSA comprises the amino acid sequence shown in SEQ ID NO: 4.

4. The α-MSH fusion protein according to claim 1, wherein the α-MSH comprises the amino acid sequence shown in SEQ ID NO: 6.

5. The α-MSH fusion protein according to claim 1, wherein the fusion protein comprises the amino acid sequence shown in SEQ ID NO: 8.

6. The α-MSH fusion protein according to claim 5, wherein the fusion protein is prepared by expression in cells of a yeast.

7. The α-MSH fusion protein according to claim 6, wherein the yeast is methylotrophic *Pichia pastoris*.

8. A method for preparation of the α-MSH fusion protein according to claim 1, wherein the method comprises steps of:
1) total gene synthesis of a sequence of α-MSH;
2) generating a sequence of PTD-HSA by polymerase chain reaction (PCR);
3) fusing the sequence of α-MSH from Step 1) and the sequence of PTD-HSA from step 2) by recombinant PCR, ligating a target fragment and a vector to obtain a recombinant yeast expression vector containing a DNA sequence of the α-MSH fusion protein;
4) transforming the recombinant yeast expression vector from Step 3) into *Escherichia coli* TOP 10 competent cells, extracting and sequencing recombinant expression vector plasmids, and then transforming plasmids whose sequences have been proved correct into a host expression system for expression, thus obtaining the fusion protein, wherein the host expression system is methylotrophic *Pichia pastoris*.

9. A recombinant expression vector comprising a DNA sequence which encodes the amino acid sequence of the α-MSH fusion protein according to claim 1.

10. A host expression system comprising the recombinant expression vector according to claim 9.

11. The recombinant expression vector according to claim 9, comprising the DNA sequence GGAGGTG-GAGGTTCTGGAGGTGGATCTGGT (SEQ ID NO: 12), wherein SEQ ID NO: 12 encodes the peptide linker L.

12. The recombinant expression vector according to claim 9, comprising the DNA sequence shown in SEQ ID NO: 1, wherein SEQ ID NO: 1 encodes the PTD.

13. The recombinant expression vector according to claim 9, comprising the DNA sequence shown in SEQ ID NO: 3, wherein SEQ ID NO: 3 encodes the HSA.

14. The recombinant expression vector according to claim 9, comprising the DNA sequence shown in SEQ ID NO: 5, wherein SEQ ID NO: 1 encodes the α-MSH.

15. The recombinant expression vector according to claim 9, comprising the DNA sequence shown in SEQ ID NO: 7, wherein SEQ ID NO: 7 encodes the α-MSH fusion protein.

16. A method of inhibiting and treating inflammatory central nervous system (CNS) diseases and disorders comprising administering the α-MSH fusion protein according to claim 1.

* * * * *